United States Patent [19]
Jonczyk et al.

[11] Patent Number: 5,866,540
[45] Date of Patent: *Feb. 2, 1999

[54] CYCLIC ADHESION INHIBITORS

[75] Inventors: Alfred Jonczyk, Darmstadt; Günter Hölzemann, Seeheim-Jugenheim; Brunhilde Felding-Habermann, Klein-Zimmern; Guido Melzer, Hofheim/Ts.; Beate Diefenbach, Darmstadt, all of Germany; David A. Cheresh, La Jolla, Calif.; Horst Kessler, Garching, Germany; Marion Gurrath, Garching, Germany; Gerhard Müller, Garching, Germany

[73] Assignee: Merck Patent Gesellschaft mit Beschrankter Haftung, Germany

[ * ] Notice: The term of this patent shall not extend beyond the expiration date of Pat. No. 5,849,692.

[21] Appl. No.: 368,760

[22] Filed: Jan. 4, 1995

Related U.S. Application Data

[63] Continuation of Ser. No. 22,024, Feb. 24, 1993, abandoned, which is a continuation-in-part of Ser. No. 909,367, Jul. 6, 1992, abandoned.

[51] Int. Cl.⁶ .............................. A61K 38/12; C07K 7/54
[52] U.S. Cl. .................................... 514/11; 514/9; 514/2; 530/317
[58] Field of Search ..................... 514/11, 9, 2; 530/317, 530/380

[56] References Cited

U.S. PATENT DOCUMENTS 5,192,746   3/1993   Lobl et al. ................................. 514/11

FOREIGN PATENT DOCUMENTS 406428   1/1991   European Pat. Off. .
410537   1/1991   European Pat. Off. .

OTHER PUBLICATIONS

The Merck Manual, 11th Ed., pp. 1055–1059 (1966).
Aumailley et al., FEBS, vol. 291, No. 1, pp. 50–54, (Oct. 1991).
Smith et al., Journal of Biological Chemistry., vol. 265, No. 21, pp. 12267–12271 (1990).
Gerhard Müller et al. "Dynamic Forcing a Method of Evaluating Activity and Selectivity Profiles of RGD (Arg–Gly–Asp) Peptides," *Angewandte Chemie, International Edition*, vol. 31, No. 3, Mar. 1992, pp. 326–328.
Stanley E. D'Souza et al., "Arginyl–glycyl–aspartic acid (RGD): A Cell Adhesion Motif" Trends in Biochemical Sciences, vol. 16, No. 7, Jul. 1991, pp. 246–250.
"Requirment of Vascular Integrin $\alpha_v\beta_3$ for Angiogenesis", Brooks et al., *Science*, 264:569–571, Apr. 1994.
"Angiogenesis Inhibitors from Scripps and Ixsys Shrink Tumors", *Genetic Technology News*, pp. 6–7, Feb. 1995.
"Scripps Research Scientists Develop New Technique for Treating Malignant Tumors", *Genetic Engineering News*, 15(2):1, Jan. 1995.
"Integrin $\alpha_v\beta_3$ Antagonists Promote Regression by Inducing . . . ", Brooks et al., *Cell*, 79:1157–1164, Dec. 1994.

*Primary Examiner*—Ponnathapura Achutamurthy
*Assistant Examiner*—T. D. Wessendorf
*Attorney, Agent, or Firm*—Millen, White, Zelano & Branigan, P.C.

[57] ABSTRACT

The present invention relates to pharmaceutical compositions which contain at least one cyclopeptide of formula I (a)–(r):

(a) cyclo(-Arg-Gly-Asp-D-Phe-Val-Ala);
(b) cyclo(-Arg-Gly-Asp-D-Phe-Leu-Ala);
(c) cyclo(-Arg-Gly-Asp-Phe-Val-D-Ala);
(d) cyclo(-Arg-Gly-Asp-Phe-Leu-D-Ala);
(e) cyclo(-Arg-Gly-Asp-D-Phe-Val-Gly);
(f) cyclo(-Arg-Gly-Asp-D-Phe-Leu-Gly);
(g) cyclo(-D-Arg-Gly-Asp-Phe-Val-Ala);
(h) cyclo(-D-Arg-Gly-Asp-Phe-Val-Gly);
(i) cyclo(-Arg-Gly-Asp-Phe-Pro-Gly);
(j) cyclo(-Arg-Gly-Asp-Phe-D-Pro-Gly);
(k) cyclo(-Arg-Gly-Asp-Phe-Pro-Ala);
(l) cyclo(-Arg-Gly-Asp-Phe-D-Pro-Ala);
(m) cyclo(-D-Arg-Gly-Asp-Phe-Val);
(n) cyclo(-Arg-D-Ala-Asp-Phe-Val);
(o) cyclo(-Arg-Gly-Asp-D-Phe-Val);
(p) cyclo(-Arg-Ala-Asp-D-Phe-Val);
(q) cyclo(-Arg-Gly-Asp-Phe-D-Val);
(r) cyclo(-Arg-Gly-D-Asp-Phe-Val);

or a salt thereof. The pharmaceutical compositions can be used as cell adhesion inhibitors, e.g., in the treatment of thrombosis, myocardial infarct, apoplexy, arteriosclerosis, inflammations, angina pectoris, and/or tumors.

3 Claims, No Drawings

CYCLIC ADHESION INHIBITORS

This application is a continuation of Ser. No. 08/022,024, filed Feb. 24, 1993, now abandoned, which application is a continuation in part of Ser. No. 07/909,367, filed Jul. 6, 1992, previously abandoned.

SUMMARY OF THE INVENTION

The present invention relates to novel pharmaceutical compositions based on cyclopeptides of the formula I(a)–(r):

I (a) cyclo(-Arg-Gly-Asp-D-Phe-Val-Ala);
(b) cyclo(-Arg-Gly-Asp-D-Phe-Leu-Ala);
(c) cyclo(-Arg-Gly-Asp-Phe-Val-D-Ala);
(d) cyclo(-Arg-Gly-Asp-Phe-Leu-D-Ala);
(e) cyclo(-Arg-Gly-Asp-D-Phe-Val-Gly);
(f) cyclo(-Arg-Gly-Asp-D-Phe-Leu-Gly);
(g) cyclo(-D-Arg-Gly-Asp-Phe-Val-Ala);
(h) cyclo(-D-Arg-Gly-Asp-Phe-Val-Gly);
(i) cyclo(-Arg-Gly-Asp-Phe-Pro-Gly); (SEQ ID NO:1)
(j) cyclo(-Agg-Gly-Asp-Phe-D-Pro-Gly);
(k) cyclo(-Arg-Gly-Asp-Phe-Pro-Ala); (SEQ ID NO:2)
(l) cyclo(-Arg-Gly-Asp-Phe-D-Pro-Ala);
(m) cyclo(-D-Arg-Gly-Asp-Phe-Val);
(n) cyclo(-Arg-D-Ala-Asp-Phe-Val);
(o) cyclo(-Arg-Gly-Asp-D-Phe-Val);
(p) cyclo(-Arg-Ala-Asp-D-Phe-Val);
(q) cyclo(-Arg-Gly-Asp-Phe-D-Val);
(r) cyclo(-Arg-Gly-D-Asp-Phe-Val);

and their physiologically compatible acid addition salts.

The abbreviations of amino acid radicals shown above and below stand for the radicals of the following amino acids Ala Alanine
Arg Arginine
Asp Aspartic acid
Gly Glycine
His Histidine
Leu Leucine
Phe Phenylalanine
Pro Proline
Val Valine.

In addition, the following have the meanings below
BOC tert.butoxycarbonyl
CBZ benzyloxycarbonyl
DCCI dicyclohexylcarbodiimide
DMF dimethylformamide
FAB fast atom bombardment
HOBt 1-hydoxybenzotriazole
M+ molion peak
OMe methoxy The compounds of formula I(a)–(r) and their physiologically compatible acid addition salts are known. They are described in FEBS Lett. 291, 50–54 (1991), the entire disclosure of which is hereby incorporated by reference. In this document, their preparation as well as their conformation analysis is described.

It is known that compounds which specifically inhibit the $\beta_3$ integrin receptor ligand interactions ("adhesion receptor antagonist," "ARA") can be used as therapeutic agents for the treatment of osteoporosis, thrombosis, myocardial infarct, arteriosclerosis, inflammations, apoplexy, angina pectoris and tumors. Furthermore, the compounds inhibit cell adhesion in the case of the formation of osteoclasts and are suitable as agents which support angiogenesis and the healing of wounds.

It was a goal of the present invention to find such ARA that can block $\beta_3$ integrin fibrinogen binding in order to provide better medicaments for the cited purposes.

Thus, it is an object of one aspect of this invention to provide novel pharmaceutical compositions which can be used as medicaments. Still other objects include methods of effecting pharmaceutical activities.

Upon further study of the specification and appended claims, further objects and advantages of this invention will become apparent to those skilled in the art.

Surprisingly, it has been found that the compounds of formula I(a)–(4) and their physiologically compatible acid addition salts have such adhesion receptor antagonistic properties which wee not mentioned for these compounds before.

The effect was found by using the method of J. W. Smith, Z. M. Ruggei, T. J. Kunicki and D. A. Cheesh descibed in J. Biol. Chem. 265, 12 267–12 271 (1990).

Details of the method are as follows:

A ninety six well untreated flat bottom plate was coated with 100 μl/well of 1 μg/ml receptor ($\alpha_{IIb\beta_e}$; $\alpha_{V\beta3}$) in coating buffer and incubated on a shaker at 4° C. overnight. The plate was washed 1× with binding buffer and then blocked with blocking buffer (100 μl/well for two hours at 30° C. After an additional washing with binding buffer, the biotinylated ligand and the competitor were added.

The ligand fibrinogen was used at a final concentration of 1 μg/ml. The competitor was added at increasing concentrations. Both ligand and competitor were added in volume of 50 μl/well at 2× of the final concentration diluted in binding buffer.

The plate was covered and incubated for three hours at 30° C. To remove unbound material the plate was washed 3× with binding buffer 100 μl/well.

Goat anti biotin antibody alkaline phosphatase conjugate (1:2000 dilution) in binding buffer was added (100 μl/well) and the plate was incubated for one hour at 30° C.

The plate was washed 3× with binding buffer, the substrate solution was added and developed in the dark at room temperature for 1–5 minutes.

The reaction was stopped by addition of 100 μl/well of 0.4M NaOH and read in the ELISA reader at 405 nm.

All points were run in triplicates. The following IC 50 values were obtained:

| Compound | IC$_{50}$ (μM) | |
|---|---|---|
| | $\alpha_{IIb\beta3}$ | $\alpha_{V\beta3}$ |
| cyclo(—Arg—Gly—Asp—D—Phe—Val—Ala) | 0.32 | 0.90 |
| cyclo(—Arg—Gly—Asp—D—Phe—Leu—Ala) | 0.76 | 1.10 |
| cyclo(—Arg—Gly—Asp—Phe—Val—D—Ala) | 1.50 | 0.25 |
| cyclo(—Arg—Gly—Asp—Phe—Leu—D—Ala) | 0.76 | 0.31 |
| cyclo(—Arg—Gly—Asp—D—Phe—Val—Gly) | 0.13 | 0.62 |
| cyclo(—Arg—Gly—Asp—D—Phe—Leu—Gly) | 0.06 | 0.54 |

-continued

| Compound | IC$_{50}$ ($\mu$M) | |
|---|---|---|
| | $\alpha_{IIb\beta3}$ | $\alpha_{v\beta3}$ |
| cyclo(—D—Arg—Gly—Asp—Phe—Val—Ala) | 22.00 | 4.50 |
| cyclo(—D—Arg—Gly—Asp—Phe—Val—Gly) | 20.50 | 1.52 |
| cyclo(—Arg—Gly—Asp—Phe—Pro—Gly); (SEQ ID NO:1) | 1.53 | 0.16 |
| cyclo(—Arg—Gly—Asp—Phe—D—Pro—Gly) | 1.50 | 1.06 |
| cyclo(—Arg—Gly—Asp—Phe—Pro—Ala); (SEQ ID NO:2) | 0.62 | 0.48 |
| cyclo(—Arg—Gly—Asp—Phe—D—Pro—Ala) | 0.74 | 0.37 |
| cyclo(—D—Arg—Gly—Asp—Phe—Val) | | |
| cyclo(—Arg—D—Ala—Asp—Phe—Val) | >100 | 52.00 |
| cyclo(—Arg—Gly—D—Asp—Phe—Val) | — | — |
| cyclo(—Arg—Gly—Asp—D—Phe—Val) | 0.60 | <0.05 |
| cyclo(—Arg—Ala—Asp—D—Phe—Val) | >100 | 0.77 |
| cyclo(—Arg—Gly—Asp—Phe—D—Val) | 0.30 | 0.05 |

The invention also relates to the use of the compounds of the formula I and their physiologically acceptable salts for the preparation of pharmaceutical formulations, in particular by non-chemical means. For this purpose, they can be converted into a suitable form of administration together with at least one solid, liquid and/or semi-liquid vehicle or auxiliary and, where appropriate, combined with one or more other active compounds.

The invention also relates to agents, in particular pharmaceutical formulations, containing at least one compound of the formula I and/or one of its physiologically acceptable salts.

These formulations can be used as medicaments in human or veterinary medicine. Suitable vehicles are organic or inorganic substances which are suitable for entered for example oral), parenteral or topical administration and which do not react with the new compounds, for example water, vegetable oils, benzyl alcohols, alkylene glycols, polyethylene glycols, glycerol triacetate, gelatine, carbohydrates, such as lactose or starch, magnesium, stearate, talc and vaseline. Tablets, pills, coated tablets, capsules, powders, granules, syrups, juices or drops are particularly used for oral administration, suppositories are particularly used for rectal administration, solutions, preferably oily or aqueous solutions, also suspensions, emulsions or implants, are particularly used for parenteral administration, and ointments, creams or powders are particularly used for topical administration. The new compounds can also be freeze-dried and the resulting lyophilizate can be used, for example, for the preparation of products for injection. The formulation indicated can be sterilized and/or contain auxiliaries, such as lubricants, preservatives, stabilizers and/or wetting agents, emulsifiers, slots to affect the osmotic pressure, buffer substances, colorants, flavorings and/or aromatic substances. If desired, they can also contain one or more other active compounds, for example one or more vitamins.

The compounds can be employed as pharmaceutical active compounds in human and veterinary medicine, in particular for the treatment and prophylaxis of thrombosis, myocardial infarct, angina pectoris, apoplexy and for tumors, that means cancer diseases.

The invention also relates to the use of the compounds of the formula I for combating diseases, in particular, and to their use for the therapeutic treatment of the human or animal body. In particular, they are inhibitors of cell adhesion, useful to inhibit, e.g., the aggregation of blood-cells and tumor-cells. Thus, the compounds can be used to inhibit adhesion in animal cells, for example, somatic cells or cancer cells of mammals.

The substances according to the invention are as a rule administered in analogy to other known commercially available peptides, but in particular in analogy to the compounds described in U.S. Pat. No. 4,472,305, preferably in dosages of about 0.05–500, in particular 0.5–100 mg per dosage unit. The daily dose is preferably about 0.01–2 mg/kg of body weight. The specific dose for each intended patient depends, however, on many different factors, for example on the activity of the specific compound employed, the age, body weight, general state of health, sex, the diet, the time and route of administration, and the rate of excretion, pharmaceutical combination and severity of the particular disorder to which the therapy applies. Parenteral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, are hereby incorporated by reference.

Preparation example 2.0 g of BOC-Arg-Gly-Asp-D-Phe-Val-Ala-OMe are dissolved in 60 ml of methanol, 1.5 ml of 2N sodium hydroxide solution are added and the mixture is stirred for 3 hours at 20°. After evaporation the residue is taken up in water, acidified to pH 3 with dilute HCl and extracted with ethyl acetate. The extract is dried over Na$_2$SO$_4$, evaporated again and the BOC-Arg-Gly-Asp-D-Phe-Val-Ala-OH obtained is stirred at 20° for 2 hours with 20 ml of 2N HCl in dioxane. The mixture is evaporated, the H-Arg-Gly-Asp-D-Phe-Val-Ala-OH obtained is dissolved in a mixture of 1800 ml of dichloromethane and 200 ml of DMF and cooled to 0°, 0.5 g of DCCI, 0.3 g of HOBt and 0.23 ml of N-methylmorpholine are added successively with stirring, and the mixture is stirred for a further 24 hours at 0° and 48 hours at 20°. The solution is concentrated and tested with a mixed bed ion exchange to free it from salts. This is then filtered off, the solution is evaporated and the residue is purified by chromatography. Cyclo(-Arg-Gly-Asp-D-Phe-Val-Ala) M$^+$: 646 FAB is obtained;

The following are obtained analogously:

cyclo(-Arg-Gly-Asp-D-Phe-Leu-Ala); M$^+$: 660;
cyclo(-Arg-Gly-Asp-Phe-Val-D-Ala); M$^+$: 646;
cyclo(-Arg-Gly-Asp-Phe-Leu-D-Ala); M$^+$: 660;
cyclo(-Arg-Gly-Asp-D-Phe-Leu-Val-Gly); M$^+$: 632;
cyclo(-Arg-Gly-Asp-D-Phe-Leu-Gly); M$^+$: 645;
cyclo(-D-Arg-Gly-Asp-Phe-Val-Ala); M$^+$: 646;
cyclo(-D-Arg-Gly-Asp-Phe-Val-Gly); M$^+$: 632;

cyclo(-Arg-Gly-Asp-Phe-Gly); (SEQ ID NO:1) $M^+$: 630;
cyclo(-Arg-Gly-Asp-Phe-Pro-Gly); $M^+$: 630;
cyclo(-Arg-Gly-Asp-Phe-Pro-Ala); (SEQ ID NO:2) $M^+$: 644;
cyclo(-Arg-Gly-Asp-Phe-Pro-Ala); $M^+$: 644;
cyclo(-D-Arg-Gly-Asp-Phe-Val); $M^+$: 575;
cyclo(-Arg-D-Ala-Asp-Phe-Val); $M^+$: 589;
cyclo(-Arg-Gly-Asp-D-Phe-Val); $M^+$: 575;
cyclo(-Arg-Ala-Asp-D-Phe-Val); $M^+$: 589;
cyclo(-Arg-Gly-Asp-Phe-D-Val); $M^+$: 575
cyclo(-Arg-Gly-D-Asp-Phe-Val); $M^+$: 575;

The examples below relate to pharmaceutical formulations which contain the compounds of the formula I or their acid addition salts.

Example A: Tablets

A mixture of 1 kg of cyclo(-Arg-Gly-Asp-D-Phe-Val-Ala) 10 kg of lactose, 6 kg of microcrystalline cellulose, 6 kg of potato starch, 1 kg of polyvinylpyrrolidone, 0.8 kg of talc and 0.1 kg of magnesium stearate is pressed into tablets in the customary manner such that each tablet contains 10 mg of active compound.

Example B: Coated tablets

Tablets are pressed analogously to Example A and are subsequently coated in the customary manner with a coating of sucrose, potato starch, talc, tragacanth and coloring substance.

Example C: Capsules

Hard gelatine capsules are filled with cyclo(-Arg-Gly-Asp-D-Phe-Val-Ala) in the customary manner such that each capsule contains 5 mg of active compound.

Example D: Ampules

A solution of 1 kg of cyclo(-Arg-Gly-Asp-D-Phe-Val-Gly) in 30 l of 1,2-propanediol is subjected to sterile filtration, and ampules are filled with the solution and subjected to sterile sealing. Each ampule contains 2 mg of active compound.

Example D: Ointment 500 mg of cyclo(-Arg-Gly-Asp-D-Phe-Leu-Gly) is mixed with 99.5 g of petroleum jelly under aseptic conditions.

Example F: Injections vials

A solution of 100 g of cyclo(-Arg-Gly-Asp-D-Phe-Leu-Gly) and 5 g of disodium hydrogenphosphate in 3 l of doubly distilled water is adjusted to pH 6.5 with 2 hydrochloric acid, sterile filtered, filled into injection vials and lyophilized under sterile conditions, and the vials are closed in a sterile manner. Each injection vial contains 5 mg of active compound.

Pharmaceutical formulations which contain one of the other active compounds of the formula and/or their physiologically acceptable acid addition salts can be obtained analogously.

The preceding examples can be repeated with similar success by substituting the generically or specifically descibed reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

---

What is claimed is:

1. A pharmaceutical composition comprising cyclo(-Arg-Gly-Asp-D-Phe-Val), cyclopeptide or a physiological salt thereof; and a pharmaceutically acceptable carrier.

2. A pharmaceutical composition according to claim 1, wherein said composition contains 0.05–500 mg of said peptide.

3. A pharmaceutical composition according to claim 1, wherein said composition contains 0.5–100 mg of said cyclopeptide.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: circular ( i i ) MOLECULE TYPE: peptide ( x i ) SEQUENCE DESCRIPTION: SEQ ID NO:1:

Arg  Gly  Asp  Phe  Pro  Gly
    1                        5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: circular ( i i ) MOLECULE TYPE: peptide ( x i ) SEQUENCE DESCRIPTION: SEQ ID NO:2:

Arg  Gly  Asp  Phe  Pro  Ala
    1                        5